(12) United States Patent
Yorkston et al.

(10) Patent No.: US 10,092,256 B2
(45) Date of Patent: Oct. 9, 2018

(54) CONE BEAM COMPUTED TOMOGRAPHY VOLUMETRIC IMAGING SYSTEM

(71) Applicant: Carestream Health, Inc., Rochester, NY (US)

(72) Inventors: John Yorkston, Penfield, NY (US); David H. Foos, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 540 days.

(21) Appl. No.: 14/397,916

(22) PCT Filed: May 17, 2013

(86) PCT No.: PCT/US2013/041487
§ 371 (c)(1),
(2) Date: Oct. 30, 2014

(87) PCT Pub. No.: WO2013/173666
PCT Pub. Date: Nov. 21, 2013

(65) Prior Publication Data
US 2015/0150524 A1 Jun. 4, 2015

Related U.S. Application Data

(60) Provisional application No. 61/648,905, filed on May 18, 2012.

(51) Int. Cl.
*A61B 6/06* (2006.01)
*H01J 35/24* (2006.01)
(Continued)

(52) U.S. Cl.
CPC ............ *A61B 6/4007* (2013.01); *H01J 35/24* (2013.01); *H01J 37/09* (2013.01); *A61B 6/032* (2013.01);
(Continued)

(58) Field of Classification Search
CPC .. H05G 1/00; H05G 1/02; H05G 1/04; H05G 1/26; H05G 1/38; H05G 1/52; H05G 1/64;
(Continued)

(56) References Cited

U.S. PATENT DOCUMENTS 4,315,157 A * 2/1982 Barnes .................... A61B 6/032
378/10
5,493,599 A * 2/1996 Mattson .................. A61B 6/032
378/147

(Continued)

FOREIGN PATENT DOCUMENTS

JP         2005288152         10/2005

OTHER PUBLICATIONS

European Search Report, dated Dec. 21, 2015, European Application No. 13790126.0, 1 page.
(Continued)

*Primary Examiner* — Anastasia Midkiff

(57) ABSTRACT

Embodiments of methods and/or apparatus for a radiographic imaging can include a plurality of x-ray sources disposed in a curve and a detector configured to revolve relative thereto. In one embodiment, a CBCT imaging method and/or apparatus can include performing a first scan at a first speed using stationary angularly distributed x-ray sources to acquire first CBCT projection data that impinge a detector of a first field of view (FOV), identifying an area of interest within the first FOV, and performing a second scan at a second speed using the x-ray sources acquire second CBCT projection data that impinge a portion of the detector of a second smaller FOV including the area of interest within the first FOV using second emissions by the x-ray sources, where the second speed is greater than the first speed.

13 Claims, 8 Drawing Sheets

(51) Int. Cl.
*H01J 37/09* (2006.01)
*A61B 6/00* (2006.01)
*A61B 6/03* (2006.01)

(52) U.S. Cl.
CPC .............. *A61B 6/06* (2013.01); *A61B 6/4085* (2013.01); *A61B 6/42* (2013.01); *A61B 6/4405* (2013.01); *A61B 6/488* (2013.01); *A61B 6/501* (2013.01); *A61B 6/54* (2013.01); *G06T 2207/10141* (2013.01); *G06T 2207/10144* (2013.01); *G06T 2207/10148* (2013.01); *G06T 2207/10152* (2013.01); *G06T 2211/412* (2013.01); *H01J 2235/162* (2013.01); *H01J 2237/045* (2013.01)

(58) Field of Classification Search
CPC .... H05G 1/70; A61B 6/00; A61B 6/02; A61B 6/03; A61B 6/032; A61B 6/035; A61B 6/04; A61B 6/0407; A61B 6/06; A61B 6/40; A61B 6/4007; A61B 6/4021; A61B 6/4085; A61B 6/42; A61B 6/44; A61B 6/4429; A61B 6/4452; A61B 6/48; A61B 6/488; A61B 6/50; A61B 6/501; A61B 6/52; A61B 6/5294; A61B 6/54; A61B 6/542; A61B 6/544; A61B 6/545; A61B 2560/00; A61B 2560/04; A61B 2560/0406; A61B 2576/00; A61B 2576/02; A61B 2576/026; G06T 1/00; G06T 1/0007; G06T 1/0014; G06T 7/00; G06T 7/70; G06T 2200/00; G06T 7/04; G06T 7/08; G06T 2207/00; G06T 2207/10; G06T 2207/10072; G06T 2207/10076; G06T 2207/10081; G06T 2207/10141; G06T 2207/10144; G06T 2207/10148; G06T 2207/10152; G06T 2207/20; G06T 2207/30; G06T 2207/30004; G06T 2207/30016; G06T 2207/30101; G06T 2210/41; G06T 2211/00; G06T 2211/40; G06T 2211/408; G06T 2211/412; G06T 2211/424; G06T 2211/432; G06T 2211/436; H01J 35/00; H01J 35/02; H01J 35/30; H01J 35/305; H01J 37/00; H01J 37/02; H01J 37/09; H01J 37/147; H01J 37/16; H01J 37/21; H01J 37/30; H01J 37/3005; H01J 37/304; H01J 37/3045; H01J 2235/00; H01J 2235/16; H01J 2235/161; H01J 2235/162; H01J 2235/163; H01J 2237/00; H01J 2237/04; H01J 2237/045; H01J 2237/0451; H01J 2237/15; H01J 2237/1505; H01J 2237/16; H01J 2237/20; H01J 2237/20292
See application file for complete search history.

(56) References Cited

U.S. PATENT DOCUMENTS

| | | | |
|---|---|---|---|
| 6,418,183 | B1 | 7/2002 | Fox et al. |
| 7,403,597 | B2* | 7/2008 | Raupach ............ A61B 6/032 378/145 |
| 2004/0228434 | A1 | 11/2004 | Tsujii |
| 2005/0226364 | A1 | 10/2005 | Bernard De Man et al. |
| 2006/0182219 | A1 | 8/2006 | Levy |
| 2006/0233295 | A1* | 10/2006 | Edic ................ A61B 6/032 378/4 |
| 2008/0080662 | A1 | 3/2008 | Shukla |
| 2008/0253516 | A1* | 10/2008 | Hui ................. A61B 6/032 378/62 |
| 2009/0225934 | A1 | 9/2009 | Hugg et al. |
| 2011/0228898 | A1 | 9/2011 | Pelc et al. |
| 2012/0108948 | A1 | 5/2012 | Jansen et al. |
| 2012/0257710 | A1* | 10/2012 | Funk ............... A61B 6/4488 378/9 |
| 2013/0343514 | A1* | 12/2013 | Heuscher ............ A61B 6/032 378/16 |

OTHER PUBLICATIONS

Ge Wang et al., "An Outlook on X-Ray CT Research and Dvelopment", Am. Assoc. Phys. Med., Section 35 (3), Mar. 2008, pp. 1051-1064.
International Search Report, dated Aug. 27, 2013, International Application No. PCT/US2013/041487, 2 pages.

* cited by examiner

CONE BEAM COMPUTED TOMOGRAPHY VOLUMETRIC IMAGING SYSTEM

CROSS REFERENCE TO RELATED APPLICATIONS

This application claims the benefit of and is a U.S. National Phase filing of PCT Application PCT/US2013/041487 filed May 17, 2013 entitled "CONE BEAM COMPUTED TOMOGRAPHY VOLUMETRIC IMAGING SYSTEM", in the names of John Yorkston and David H. Foos, which claims the benefit of U.S. Provisional Application U.S. Ser. No. 61/648,905, provisionally filed on May 18, 2012, entitled "CONE BEAM COMPUTED TOMOGRAPHY VOLUMETRIC IMAGING SYSTEM", in the name of John Yorkston, all of which are incorporated herein by reference in their entirety.

FIELD OF THE INVENTION

The invention relates generally to the field of digital imaging, and in particular to medical digital radiographic imaging.

BACKGROUND

It is desirable to quickly evaluate patients suspected of having a stroke. Indeed, some medical practitioners believe that a fast evaluation of the type and severity of the condition is extremely important.

SUMMARY

It is an aspect of this application to address in whole or in part, at least the foregoing and other deficiencies in the related art.

It is another aspect of this application to provide in whole or in part, at least the advantages described herein.

Another aspect of this application is to provide radiographic image methods and/systems that can address stroke diagnosis.

Another aspect of this application is to provide methods and/systems that can provide volumetric imaging systems and/or methods that can have a smaller footprint and/or simpler mechanical design than CT (computed tomography) systems having a slip ring technology.

Another aspect of this application is to provide methods and/systems that can provide volumetric imaging systems and/or methods that can include multi-functional capability.

Another aspect of this application is to provide methods and/systems that can provide volumetric imaging systems and/or methods that can include a digital detector revolving separately and/or powered separately from a radiation source.

In accordance with one embodiment, the present invention can provide a method of performing radiographic examination by a radiographic CT imaging system, the radiographic CT imaging system to include a plurality of x-ray sources disposed in a curve and a detector configured to revolve relative to the plurality of x-ray sources, the radiographic examination method can include performing a first scan at a first speed using the plurality of x-ray sources and the detector to acquire first CT projection data of a first field of view (FOV) of an object using first emissions by the plurality of x-ray sources that impinge the detector, identifying a plane of interest within the first FOV, performing a second scan at a second speed using the plurality of x-ray sources and the detector to acquire second CT projection data of a second smaller FOV including the plane of interest within the first FOV using second emissions by the plurality of x-ray sources that impinge a portion of the detector, where the second speed is greater than the first speed; and outputting the data of the first CT projection data and the second CT projection data from the detector.

In accordance with one embodiment, the present invention can provide a radiographic CT imaging system, can include a plurality of x-ray source emissions disposed in a curve, a battery powered detector configured to revolve relative to the plurality of x-ray source emissions, and at least one spatial restriction device to limit a cross-section of the plurality of x-ray source emissions, where the plurality of x-ray source emissions, the detector and the at least one spatial restriction device are configured in both of (i) a first configuration to obtain a first field of view (FOV) of first emissions of the curved x-ray source emissions that impinge the detector and (ii) a second configuration to obtain a second smaller FOV of second emissions of the curved x-ray source emissions that impinge the detector, and where the first emissions and the second emissions determine a volumetric image of an overlapping FOV.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DESCRIPTION OF EXEMPLARY EMBODIMENTS

Figure 1:
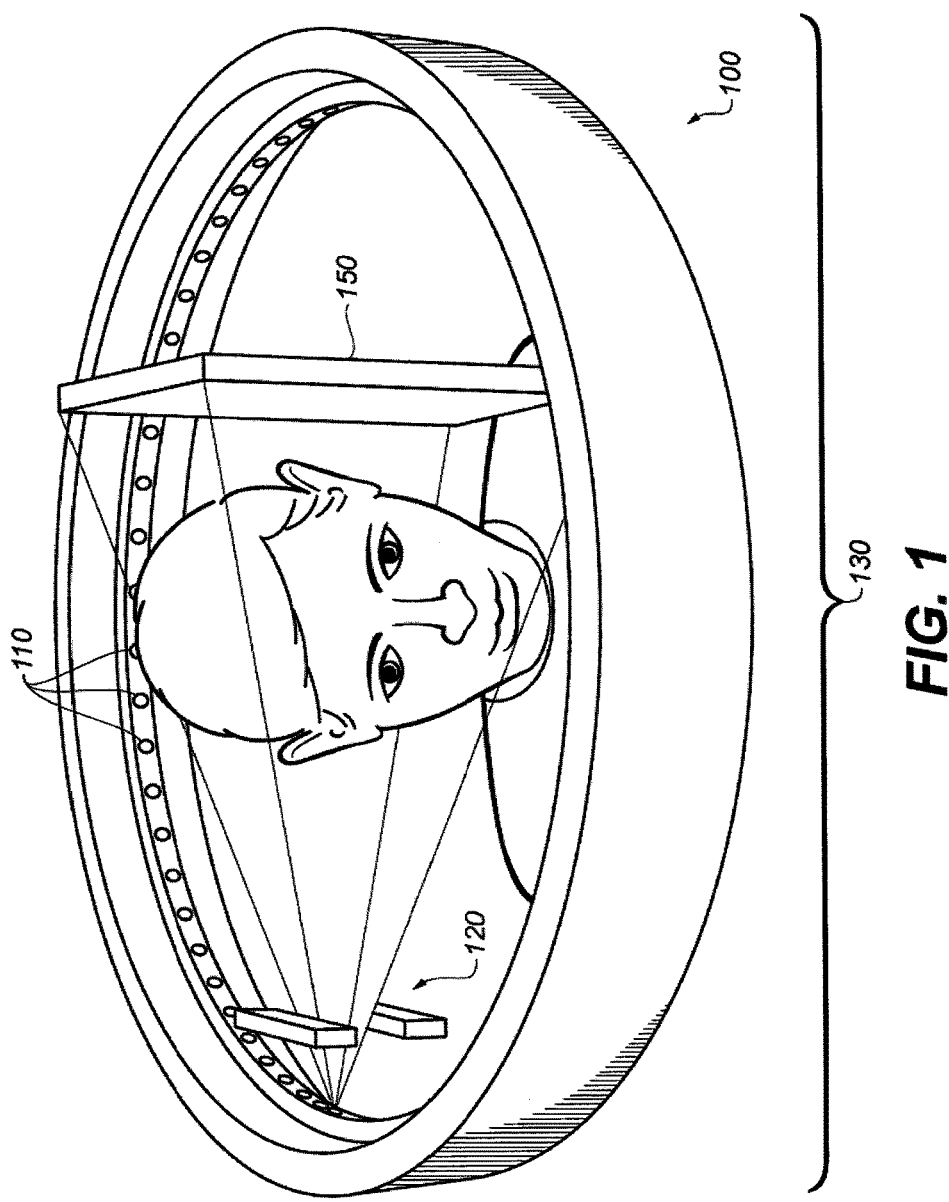
FIG. 1 is a diagram showing a volumetric imaging system embodiment can be configured as a Cone Beam Computed Tomography (CBCT) system according to the application.

Priority is claimed from commonly assigned, copending U.S. provisional patent applications Ser. No. 61/648,905, filed May 18, 2012, entitled "CONE BEAM COMPUTED TOMOGRAPHY VOLUMETRIC IMAGING SYSTEM", in the name of John Yorkston, the disclosure of which is incorporated by reference.

The following is a detailed description of exemplary embodiments of the invention, reference being made to the drawings in which the same reference numerals identify the same elements of structure in each of the several figures.

One current stroke evaluation practice is to perform two different CT scans (e.g., using slip ring technology). The first CT scan is conducted without a contrast agent so as to evaluate "bleeding" or blockage. The second CT scan is conducted with a contrast agent so as to quantitatively measure blood/contrast uptake and outflow.

This second CT scan can be accomplished using several individual CT scans performed a number of seconds apart, acquired over a number of minutes. For example, the second CT scan can include a plurality of individual comparative CT scans conducted repeatedly at a first interval (e.g., repeatedly, periodically such as every 30 seconds) during a full period or second interval (e.g., several or 5 minutes) to evaluate the progression of the contrast (e.g., severity and condition of the stroke) over the second interval. However, the capture of such individual scans requires high speed acquisition of data from multiple angles to allow reconstruction of pathologic features that are changing with time (e.g., the distribution of the contrast agent).

Current CT systems (e.g., using slip ring technology) may be considered by some practitioners to be bulky and expensive for use in an Emergency Room. So the typical workflow to obtain CT scans is for the patient to be transported to a radiology area for the CT scans.

Applicants have recognized that it would be advantageous to be able to perform these two different CT scans in the emergency room to speed the evaluation process of the patient.

This disclosure describes exemplary embodiments of volumetric radiographic imaging systems and/or methods, suitable for head imaging and having an imaging capability sufficient to allow at least evaluation of a stroke patient's condition (e.g., accurately, rapidly and/or without removal from an emergency treatment area).

Exemplary embodiments of volumetric imaging systems do not include a slip ring technology. Such volumetric imaging systems can then have a smaller footprint and/or simpler mechanical design than CT systems having a slip ring technology. In one embodiment, a volumetric imaging system embodiment can be configured as a CBCT system. If desired, a volumetric imaging system embodiment can include a multi-functional capability, for example, to acquire standard projection radiographs of the patient's head, and/or provide fluoroscopic imaging capabilities. While suited for head imaging, embodiments of volumetric imaging systems and/or methods can image a body or other body parts of a size able to fit within the bore of the device (such as an extremity).

In one exemplary embodiment, a volumetric imaging system is configured using a ring of x-ray sources. For example, approximately 300 to 600 sources arranged in an arc or circle having a diameter of about 1 meter. The x-ray sources can be mounted with a high speed, large area digital detector and a collimation system that provides adjustment of the x-ray field incident on the patient and digital detector. The diameter of the bore of the volumetric imaging system embodiment would be of sufficient size/opening to provide comfortable and/or ready access for a patient's head in a vertical position, angled position, supine or prone position (for example, laying on a stretcher). The patient's head can be cradled in/on a support (such as a support plate) that compliments/mates into the volumetric imaging system embodiment (e.g., system's bore). The large area digital detector and collimation system can operate by rotating around the patient while the stationary x-ray sources fire/activate sequentially.

In one embodiment, a disclosed volumetric imaging system can be configured as a Cone Beam Computed Tomography (CBCT) system. With such an exemplary CBCT system configuration, to obtain a full CBCT volume of the patient's head, the collimation system would be arranged such that the digital detector is illuminated with x-rays (e.g., intended to cover or having passed though an entirety of a patient's head) and the digital detector can be rotated through at least 180 degrees plus a "fan angle" at a speed consistent with acquisition of sufficient 2D projections to allow full 3-dimensional reconstructions of sufficient image quality for the medical practitioner to provide an evaluation of the patient's head or body part. For example, to address the medical practitioner's questions surrounding the issue of bleeding. The rotational speed can be determined by the data acquisition rate of the large area digital detector. In one embodiment, such an examination can be used to evaluate stroke "bleeding" or "blockage" described above relative to a first CT scan of two different CT scans. This is illustrated in FIG. 1.

More particularly, FIG. 1 illustrates a volumetric imaging system embodiment having a CBCT configuration. As shown in FIG. 1, a CBCT system embodiment 100 configuration can include a stationary circular array of x-ray sources 110 (e.g., source ring), a beam collimator 120, and a large area digital detector 150 (e.g., portable, wireless, untethered). The digital detector 150 can rotate at a suitable speed to acquire full head data of the patient.

Once the volume (whether a full or partial volume) is acquired and reconstructed, the medical practitioner can identify a particular or more limited region of interest (ROI) of the patient. Embodiments of volumetric imaging systems herein can adjust the collimation and detector readout region, source radiation control and/or the relative location of the patient's position within a bore 130 (e.g., imaging area) to control/limit the acquisition to this identified ROI. This is illustrated in FIG. 2.

Figure 2:
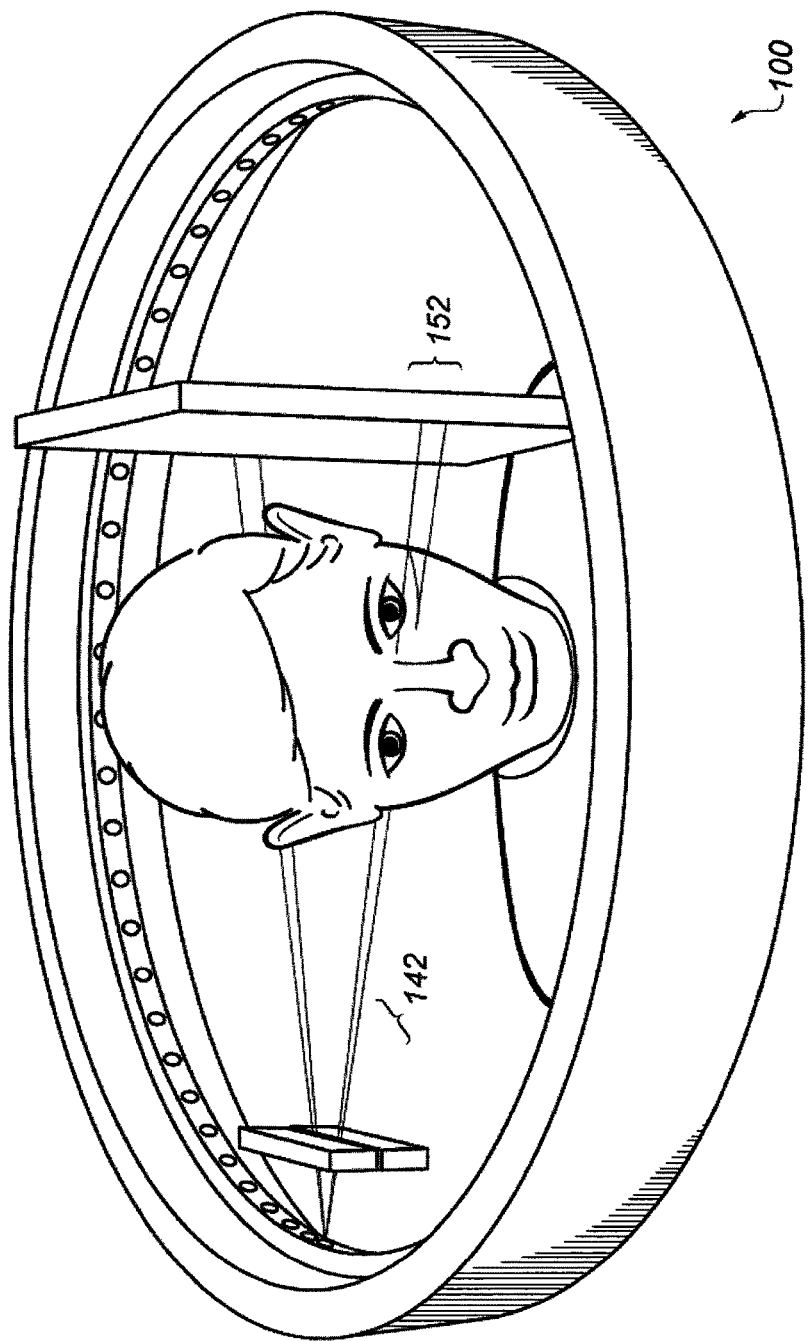
FIG. 2 is a block diagram showing a volumetric imaging system embodiment in a narrow slice configuration (e.g., fan beam, stripe) that can use a collimated x-ray beam and/or small readout section of the detector according to the application.

For example, FIG. 2 illustrates a volumetric imaging system embodiment 100 in a narrow slice configuration (e.g., fan beam, stripe) showing a collimated x-ray beam and small readout section 152 of the detector 150. As shown in FIG. 2, an emitted beam from an exemplary one of the x-ray sources 110 can be collimated to a thin slice 142 and detected by a small readout section 152 of the detector 150. The detector 150 rotates at a fast rate (for example, approximately 2-3 rev/sec) to acquire thin CT slice data. However, the detector 150 can rotate at faster speeds as desired for specific configurations. In one embodiment, a total acquisition time for exemplary thin CT slice data can be 1-10 seconds. In one embodiment, the detector 150 can move (e.g. within the total acquisition time) to use different portions of an imaging area of the detector 150 to receive radiation to generate the thin CT slice data. Although, the small readout section 152 is shown as a thin horizontal slice of the detector, the small readout section 152 can be configured to use other shapes including vertically oriented slices or rectangles, polygons, spheres, squares, closed loops, pyramids, or the like.

Using a smaller section of the digital detector 150 (such as shown in FIG. 2) provides a more rapid acquisition of the range of angular data required to reconstruct the region of interest. The digital detector 150 can rotate at a high rate of speed (for example, approximately 2-3 rev/sec) during this acquisition phase. This high rate of rotational speed and/or reading from a smaller section of the detector 150 can allow a more accurate determination of the temporal development of the clinical information required for diagnosis. In one embodiment, such an examination can be used to repeatedly evaluate "contrast disbursement" for a period as described above relative to a second CT scan of two different CT scans for stroke evaluation.

Figure 3:
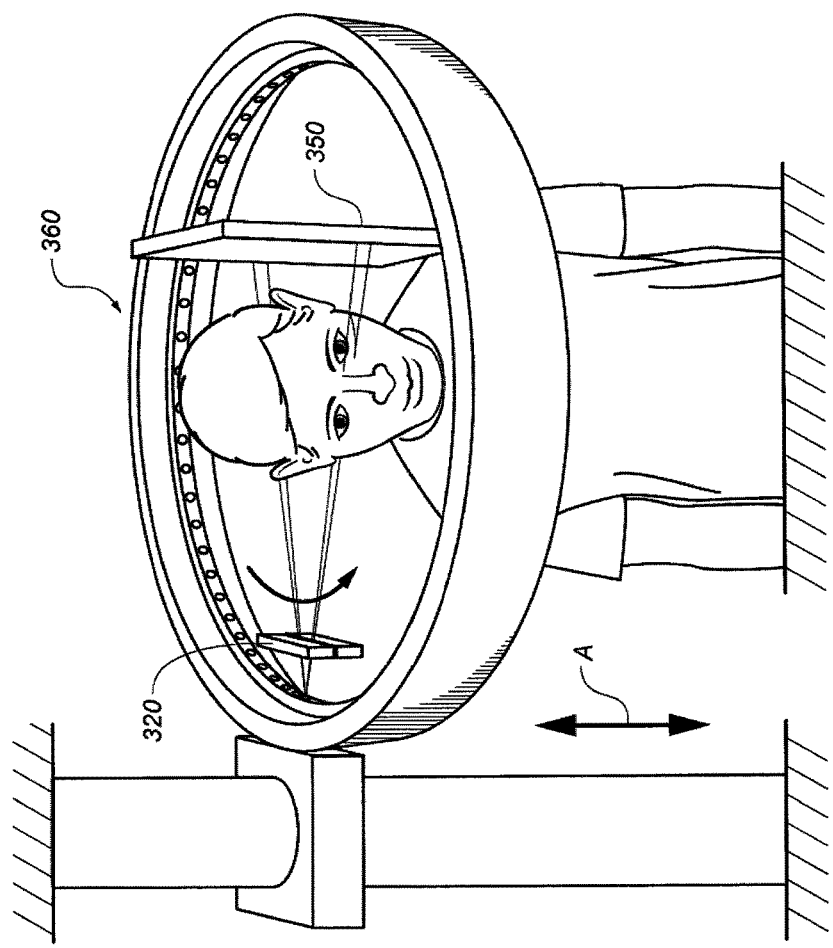
FIG. 3 is a diagram showing a translation of the imaging assembly (e.g., comprised of the source ring, digital detector, and beam collimator) relative to a stationary object to be imaged for a volumetric imaging system embodiment according to the application.

In situations where an extended/larger region of the patient (e.g., object) is be imaged, it is possible to translate the source ring, digital detector, and beam collimator along the patient's body axis. In one arrangement, generally illustrated in FIG. 3, the translation of the imaging assembly (e.g., comprised of the source ring, digital detector, and beam collimator) relative to a stationary patient allows the acquisition of a spiral CT set of data. An imaging assembly 360 can translate along an axis substantially parallel to the patient (shown at A; which is substantially perpendicular to the arc of rotation) so as to acquire the image data relative to the stationary patient. The imaging assembly 360 can translate in a single direction or can reciprocally move in opposite directions (e.g., relative to the patient) in consecutive or subsequent translations. As the imaging assembly 360 translates, a digital detector 350 and beam collimator 320 rotate corresponding to sequentially firing x-ray sources so as to acquire the image data relative to the stationary patient. With the translation and/or rotation movements of the various components, the resulting data set is spiral (e.g., helical or includes angular combined with vertical movement). In one embodiment, the extent of the translation (e.g., portion of the head or body to be imaged) by the x-ray fan beam can be automatically determined (e.g., by the volumetric imaging system, input by an operator, etc.) based on the first examination or CBCT volume of the patient's head or body part.

Figure 4:
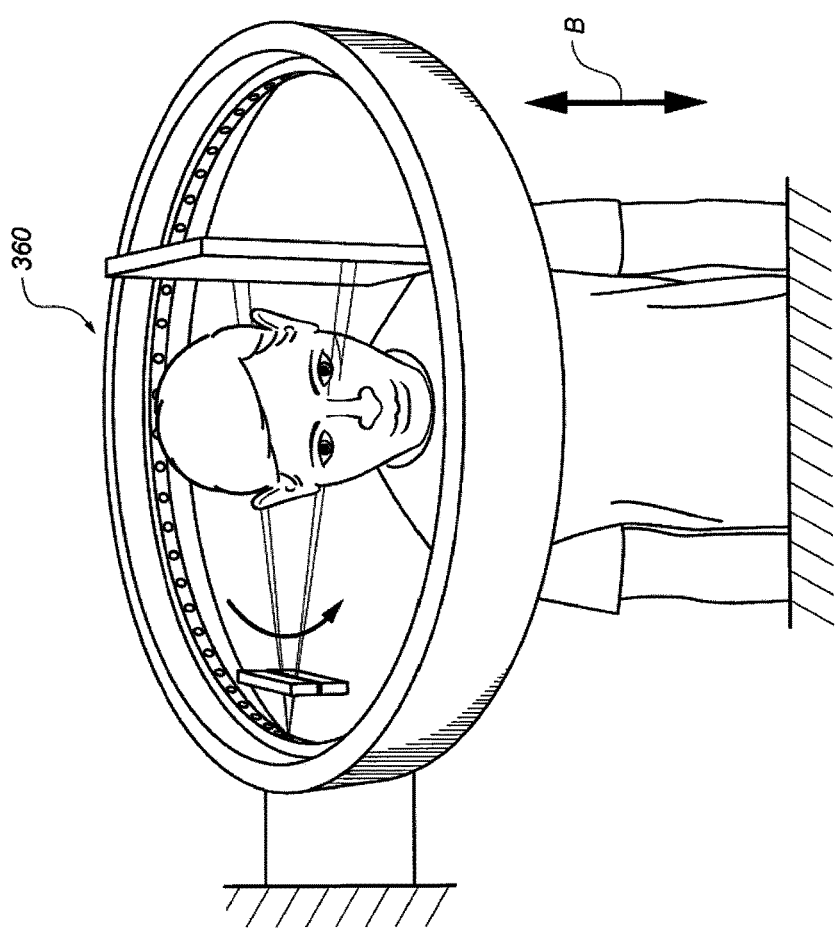
FIG. 4 is a diagram showing a translation of an object to be imaged relative to a stationary imaging assembly (e.g., comprised of the source ring, digital detector, and beam collimator) according to the application.

Alternatively, an imaging assembly can remain stationary (e.g., at a fixed location) and the patient can be translated. This arrangement is generally illustrated in FIG. 4 where the imaging assembly 360 is fixed and the patient translates (shown at arrow B) relative to the imaging assembly 360. The translation of the patient can be accomplished for example by means of a gurney. In this arrangement, the digital detector and beam collimator rotate but do not translate. In one embodiment, the volumetric imaging system can be configured as a ring of a plurality of stationary x-ray sources.

Figure 5:
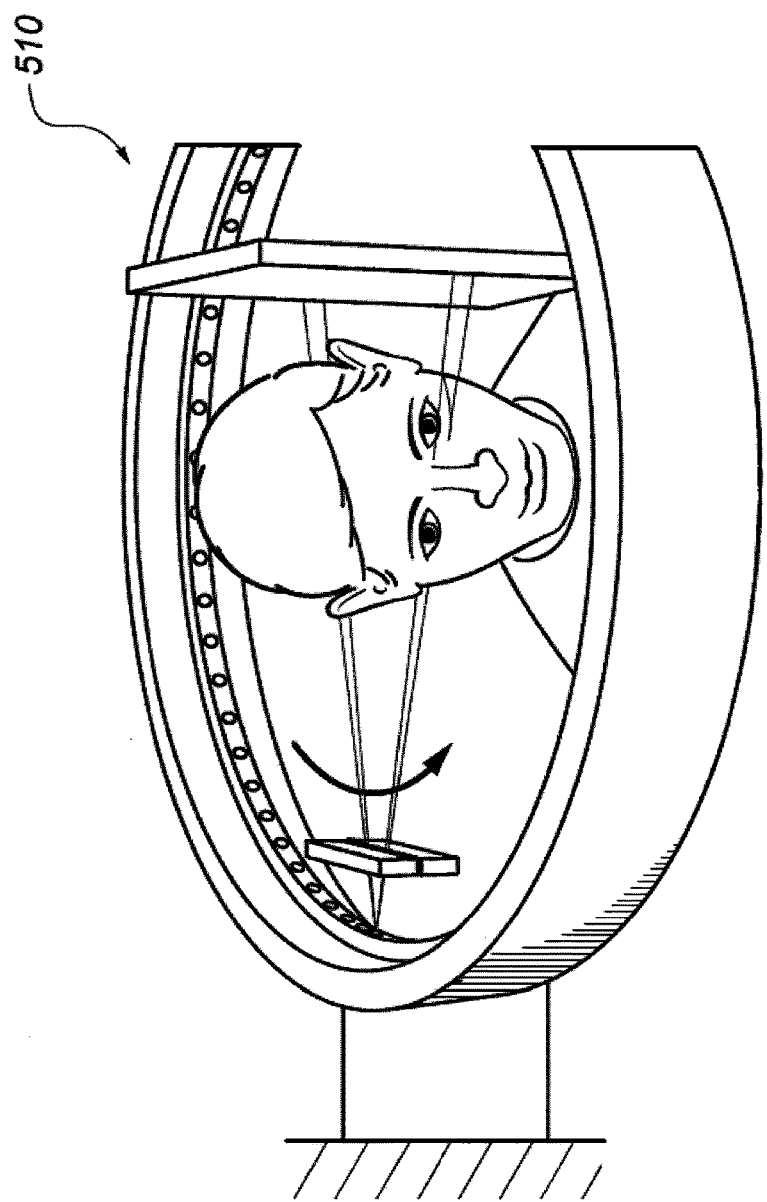
FIG. 5 is a diagram showing another volumetric imaging system embodiment including a plurality of x-ray sources configured as an arc (e.g., less than 360 degrees) according to the application.

While FIGS. 1-4 illustrate a 360 degree ring of x-ray sources, volumetric imaging system embodiments can be configured to operate within less than 360 degrees. For example, one system can be configured generally as an arc (i.e., less than 360 degrees) such as illustrated in FIG. 5. As shown in FIG. 5, an imaging assembly can include a source ring 510 in the form of an arc. With such an arrangement, the system can include either a single x-ray source which moves within the arc, or a plurality of stationary x-ray sources disposed along the arc.

Figure 6:
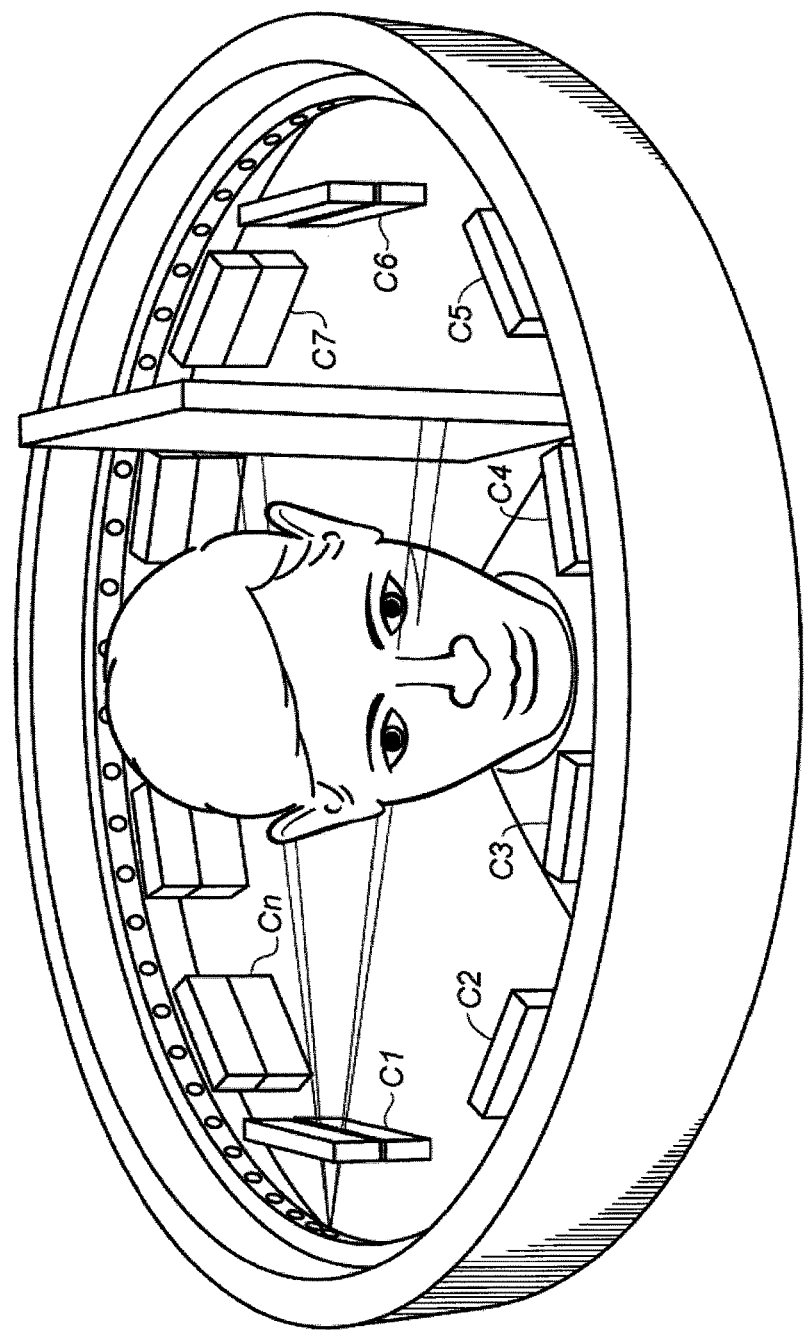
FIG. 6 is a diagram showing another volumetric imaging system embodiment including a plurality of collimators according to the application.

FIGS. 1-5 illustrate exemplary imaging systems and/or methods that can use a single beam collimator that can rotate, and as such, can operate with each x-ray source of the source ring to form associated collimated x-ray beams. In an alternative arrangement, the system can include a plurality of collimators (C1, C2, through Cn), as illustrated in FIG. 6. As shown in FIG. 6, an exemplary system includes a ring of collimators disposed adjacent the ring of x-ray sources, wherein an x-ray source is paired with a collimator (C1, C2, through Cn). In operation, each x-ray source is activated wherein it emits x-rays through its adjacent collimator to emit a collimated x-ray beam (e.g., to impinge the detector). In one arrangement, the plurality of collimators is stationary relative to the ring of x-ray sources. In one embodiment, each of the plurality of collimators (e.g., stationary) can cooperate with more than one of the x-ray sources.

In another arrangement, the system can include a stationary plurality of collimators to cooperate with a single rotating x-ray source (e.g., one or more rotating x-ray source). For example, the single rotating x-ray source can be battery powered and receive (e.g., wireless communications) instructions regarding emission characteristics, speed of rotation, spatial emission control (e.g., collimation) and the like. In operation, the x-ray source is rotated about an arc or source ring, and is activated when it is adjacent one of the stationary collimators.

In one embodiment, only a digital detector revolves to acquire the image data as a radiation imaging assembly translates relative to the (e.g., stationary) object to be imaged. For example, one volumetric imaging system embodiment is configured to sequentially activate selected ones of a ring of x-ray sources spatially collimated to a fan as the detector rotates around the patient. In one embodiment, the source ring and/or the detector can be enclosed in separate housings. Further, for example, one embodiment can include a continuous integral collimator and use pulsed emissions by the x-ray source ring.

Amorphous silicon flat panel digital detectors have been shown to be suited for the equivalent of thousands of frames per second for limited readout sections (e.g., slices, stripes, prescribed ROIs). CMOS type digital detectors can also operate at sufficiently high readout rates to be suitable. Solid state digital radiographic detectors can be used. To further enhance image acquisition, it may be desirable to acquire dual energy data by modifying the energy of the x-ray sources during the x-ray acquisition. For example, alternate x-ray sources (e.g., in the x-ray source ring) could use different dual energy for detection. This would allow segmentation of the iodine contrast signal to improve the accuracy of the quantitative evaluation of the data. In one embodiment, physical locations of at least three different emission characteristic x-ray sources can have a prescribed sequence, or alternatively, one or more x-ray sources can emit at three or more multiple energy levels (e.g., kVp and/or mA) in prescribed sequences. In one embodiment, an emission level of the plurality of x-ray sources (e.g., an energy level) can correspond to the contrast agent. In one embodiment, a set of emission levels of the plurality of x-ray sources (e.g., energy levels) can be selected to increase or optimize visualization to the contrast agent in 2D or 3D images from the detector. Thus, multiple energy data can be acquired by positioning differing x-ray sources or variably driving individual x-ray sources to emit at a plurality of energy levels (or combinations thereof) in a manner similar to such dual energy embodiments for volumetric imaging system embodiments described herein.

With some embodiments of a disclosed volumetric imaging system, the x-ray sources are stationary and the digital detector and collimation system rotate in an arc or circular orbit, ranging from zero to 360 degrees.

To reduce the complexity of the system design, one configuration would employ carbon nano-tube sources for the circular x-ray source. Such carbon nano-tube sources are being developed for various medical applications (e.g., XinRay and XinTek).

Another configuration would reduce the complexity of the rotating mount for the large area detector. This configuration would include a battery powered detector that would obviate the necessity of slip ring technology for distribution of power and data. A suitable battery powered detector (e.g., portable detector) would be Carestream Health's DRX-1 detector comprising enhanced imaging readout capabilities.

In certain embodiments disclosed herein, a detector or portable detector can be removed from a volumetric imaging system (e.g., for use with other radiographic imaging systems). Further, a detector or portable detector can be replaced (e.g., for recharging) in a volumetric imaging system to allow increased use of the volumetric imaging system.

An exemplary digital battery powered detector could also be wireless which would allow realtime offloading of the data for fast reconstruction by a remote workstation, semi-realtime offloading of the data, or alternatively the digital detector could store the projection slices/regions in on board memory during acquisition and then transmit the data at a slower speed either during the acquisition or after the acquisition was complete.

Alternatively, the digital detector could stop rotation, align with a data connection positioned at a specific angular location and offload the data through an infrared/microwave/wired connection. While the volumetric imaging system is not being used for imaging, this connection can be used to charge the battery of the digital detector. Depending on the ramp-up and ramp-down speed of the rotational motion, the detector may stop between different temporal acquisitions of the specific ROI data, or it may keep rotating until the full exam/scan is completed.

Applicants have described embodiments of volumetric imaging systems and/or methods that can acquire a traditional CBCT data set of a patient's head, and/or then control or collimate an x-ray beam to a narrow slice, and a series of high speed slice acquisitions are taken that allows evaluation of a contrast agent perfusion in a portion of or throughout the patient's head. One system comprises an angularly distributed radiation source such as a stationary ring or spline of x-ray sources, such as carbon nano-tube sources.

Although described variously as angular displaced/distributed x-ray source(s) or plurality of x-ray sources disposed at a ring, arc, or circular arrangement, embodiments herein can include but are not limited to a 3D path, curve, arcuate arrangement, spline or the like, as desired for configuration of an x-ray source path or arrangement for the plurality of x-ray sources described herein for volumetric imaging systems and/or methods for using the same.

There has been described volumetric imaging systems for imaging a patient, wherein the system comprises at least one x-ray source, at least one detector, and at least one emission control device (e.g., collimator).

In arrangement A, the system comprises:
a plurality of x-ray sources disposed in an arc;
a single detector to rotate relative to the arc; and
a single collimator disposed inboard of the plurality of x-ray sources, the collimator being positioned intermediate the x-ray sources and the detector, the collimator being rotatable relative to the arc in coordinated operation with the x-ray sources to emit a collimated beam of x-rays toward the detector.

With arrangement A-A, the x-ray sources, detector, and collimator are translated in a direction substantially perpendicular to the arc of rotation. In this arrangement, the patient is stationary. With arrangement A-B, the x-ray sources, detector, and collimator are not translated. Rather, the patient is translated in a direction substantially perpendicular to the arc of rotation.

In arrangement B, the system comprises:
a plurality of x-ray sources disposed in a curve;
a single detector to rotate relative to the curve; and
at least one or a plurality of stationary collimators disposed inboard of the plurality of x-ray sources, each collimator being associated with one or more of the plurality of x-ray sources, each collimator operating in coordination with its associated x-ray source to collimate a beam of x-rays toward the (patient) detector.

With arrangement B-A, the x-ray sources, detector, and collimators are translated in a direction substantially perpendicular to the arc of rotation. In this arrangement, the patient is stationary. With arrangement B-B, the x-ray sources, detector, and collimators are not translated. Rather, the patient is translated in a direction substantially perpendicular to the arc of rotation.

In arrangement C, the system comprises:
a single x-ray source which rotates relative to an arc;
a single detector which rotates relative to the arc; and
a plurality of stationary collimators disposed inboard of the x-ray source, the x-ray source operating in coordination with each collimator to emit a collimated beam of x-rays toward the patient and detector.

With arrangement C-A, the x-ray source, detector, and collimators are translated in a direction substantially perpendicular to the arc of rotation. In this arrangement, the patient is stationary. With arrangement C-B, the x-ray source, detector, and collimators are not translated. Rather, the patient is translated in a direction substantially perpendicular to the arc of rotation.

In arrangement D, the system comprises:
at least one angularly displaceable x-ray source;
a detector configured to revolve relative to the at least one angularly displaceable x-ray source; and
at least one spatial restriction device for the at least one angularly displaceable x-ray source,
where the at least one angularly displaceable x-ray source, the detector and the at least one spatial restriction device are configured in both of a first configuration to obtain a first field of view (FOV) of first emissions by the x-ray source that impinge the detector and a second configuration to obtain a second FOV of second emissions by the by the x-ray source that impinge the detector, where the second FOV is smaller than the first FOV, and where the first emissions and the second emissions determine a volumetric image of an overlapping FOV.

In one embodiment, a method of diagnosing a stroke in a patient can use a radiographic CT imaging system, the radiographic CT imaging system to include a plurality of x-ray sources disposed in a curve and a detector configured to revolve relative to the plurality of x-ray sources, the method comprising performing a first scan at a first speed using the plurality of x-ray sources and the detector to acquire first CT projection data of a first field of view (FOV)

of an object using first emissions by the plurality of x-ray sources that impinge the detector; performing a second scan at a second speed using the plurality of x-ray sources and the detector to acquire second CT projection data of a second smaller FOV within the first FOV using second emissions by the plurality of x-ray sources that impinge a portion of the detector, where the second speed is greater than the first speed; and comparing the volumetric images to determine a medical condition (e.g., contusion or stroke).

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

It should be noted that embodiments of a digital or portable detector described herein can use direct or indirect image sensing of impinging radiation. For example, image sensing by the detector can be performed by direct detection, in which case the image-sensing element directly absorbs X-rays and converts them into charge carriers. However, in most commercial digital radiography systems, indirect detection is used by the detector, in which an intermediate scintillator element converts the X-rays to visible-light photons that can then be sensed by a light-sensitive image-sensing element. Further, photon counting pixel elements can be used in exemplary image sensing by the detector.

CBCT Apparatus

Computed tomography (CT) imaging apparatus, Cone Beam (CB) CT imaging apparatus, and imaging algorithms used to obtain 3-D volume images using such systems are well known in the diagnostic imaging art and are, therefore, not described in detail in the present application.

In typical applications, a computer or other type of dedicated logic processor for obtaining, processing, and storing image data is part of the CBCT system, along with one or more displays for viewing image results. A computer-accessible memory is also provided, which may be a non-volatile memory storage device used for longer term storage, such as a device using magnetic, optical, or other data storage media. In addition, the computer-accessible memory can comprise an electronic memory such as a random access memory (RAM) that is used as volatile memory for shorter term data storage, such as memory used as a workspace for operating upon data or used in conjunction with a display device for temporarily storing image content as a display buffer, or memory that is employed to store a computer program having instructions for controlling one or more computers to practice method and/or system embodiments according to the present application.

Figure 7:
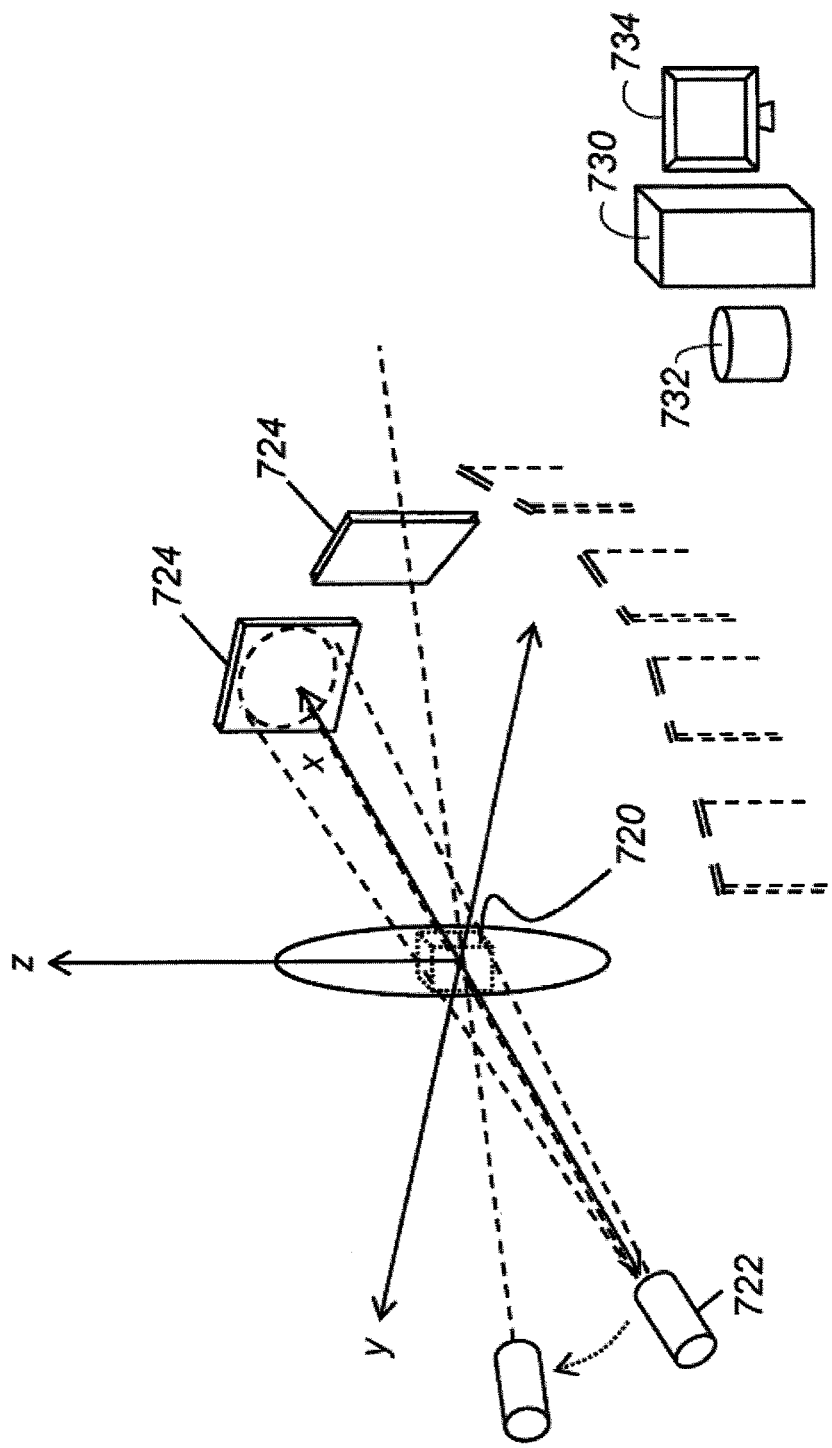
FIG. 7 is a schematic diagram showing components and architecture used for conventional CBCT scanning.

Referring to the perspective view of FIG. 7, there is shown, in schematic form and using exaggerated distances for clarity of description, the activity of an exemplary conventional CBCT imaging apparatus for obtaining the individual 2-D images that are used to form a 3-D volume image. A radiation source 722 directs radiation through a beam shaping apparatus (not shown) toward a subject 720, such as a patient or other imaged subject. A sequence of images of subject 720 is obtained in rapid succession at varying angles about the subject over a range of scan angles, such as one image at each 1-degree angle increment in a 360-degree orbit. A DR detector 724 is moved to different imaging positions about subject 720 in concert with corresponding movement of radiation source 722. For example, such corresponding movement can have a prescribed 2D or 3D relationship. FIG. 7 shows a representative sampling of DR detector 724 positions to illustrate how these images are obtained relative to the position of subject 720. Once the needed 2-D projection images are captured in a prescribed sequence, a suitable imaging algorithm, such as FDK filtered back projection or other conventional technique, can be used for generating the 3-D volume image. Image acquisition and program execution are performed by a computer 730 or by a networked group of computers 730 that are in image data communication with DR detectors 724. Image processing and storage is performed using a computer-accessible memory in image data communication with DR detectors 724 such as computer-accessible memory 732. The 3-D volume image or exemplary 2-D image data can be presented on a display 734.

Figure 8:
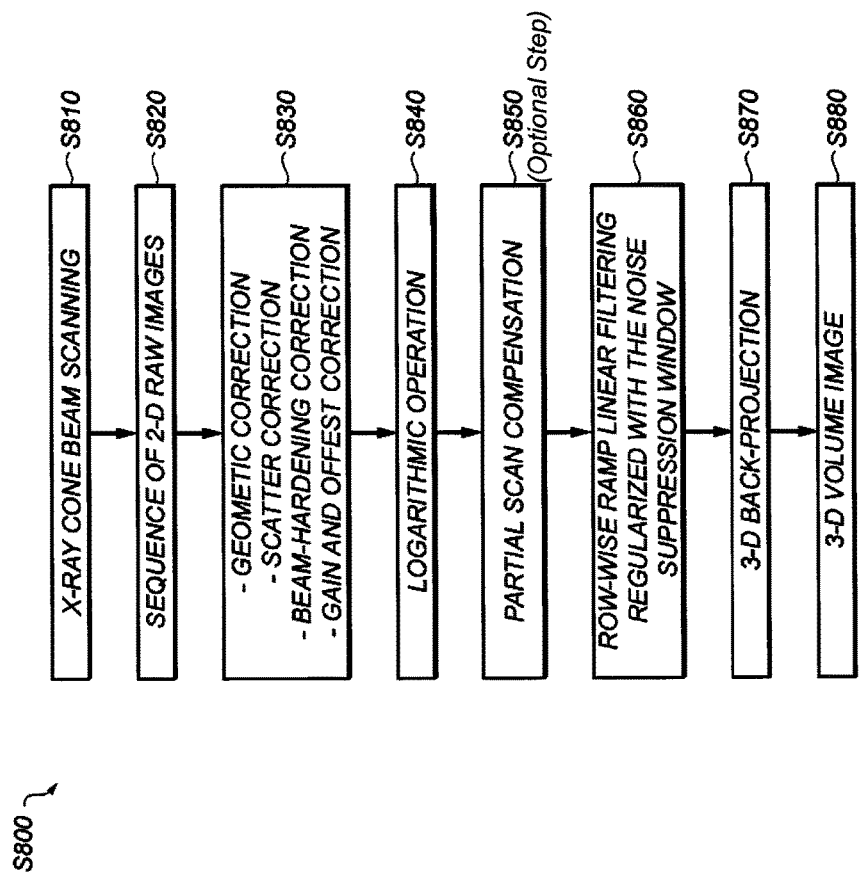
FIG. 8 is a logic flow diagram showing the sequence of processes used for conventional CBCT volume image reconstruction.

The logic flow diagram of FIG. 8 shows a conventional image processing sequence S800 for CBCT reconstruction using partial scans. A scanning step S810 directs cone beam exposure toward the subject, enabling collection of a sequence of 2-D raw data images for projection over a range of angles in an image data acquisition step S820. An image correction step S830 then performs standard processing of the projection images such as but not limited to geometric correction, scatter correction, gain and offset correction, and beam hardening correction. A logarithmic operation step S840 obtains the line integral data that is used for conventional reconstruction methods, such as the FDK method well-known to those skilled in the volume image reconstruction arts.

An optional partial scan compensation step S850 is then executed when it is necessary to correct for constrained scan data or image truncation and related problems that relate to positioning the detector about the imaged subject throughout the scan orbit. Optional step S850 can be used for CBCT where typically a limited or partial angular scan (e.g., 220-degrees or 180-degrees plus fan angle) can be used. A ramp filtering step S860 follows, providing row-wise linear filtering that is regularized with the noise suppression window in conventional processing. A back projection step S870 is then executed and an image formation step S880 reconstructs the 3-D volume image using one or more of the non-truncation corrected images. FDK processing generally encompasses the procedures of steps S860 and S870. The reconstructed 3-D image can then be stored in a computer-accessible memory and displayed.

In the context of the present disclosure, the term "code value" can refer to the value that is associated with each volume image data element or voxel in the reconstructed 3-D volume image. The code values for CBCT images are often, but not always, expressed in Hounsfield units (HU).

Embodiments of radiographic imaging systems and/or methods described herein contemplate methods and program products on any computer readable media for accomplishing its operations. Certain exemplary embodiments accordingly can be implemented using an existing computer processor, or by a special purpose computer processor incorporated for this or another purpose or by a hardwired system.

Consistent with exemplary embodiments, a computer program with stored instructions that perform on image data accessed from an electronic memory can be used. As can be appreciated by those skilled in the image processing arts, a computer program implementing embodiments herein can be utilized by a suitable, general-purpose computer system, such as a personal computer or workstation. However, many other types of computer systems can be used to execute computer programs implementing embodiments, including networked processors. Computer program for performing method embodiments or apparatus embodiments may be stored in various known computer readable storage medium (e.g., disc, tape, solid state electronic storage devices or any other physical device or medium employed to store a computer program), which can be directly or indirectly connected to the image processor by way of the internet or other communication medium. Those skilled in the art will readily recognize that the equivalent of such a computer program product may also be constructed in hardware. Computer-accessible storage or memory can be volatile, non-volatile, or a hybrid combination of volatile and non-volatile types.

It will be understood that computer program products implementing embodiments of this application may make use of various image manipulation algorithms and processes that are well known. It will be further understood that computer program products implementing embodiments of this application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program product implementing embodiments of this application, are not specifically shown or described herein and may be selected from such algorithms, systems, hardware, components and elements known in the art.

While the application has been illustrated with respect to one or more implementations, alterations and/or modifications can be made to the illustrated examples without departing from the spirit and scope of the appended claims. In addition, while a particular feature of the invention can have been disclosed with respect to at least one of several implementations/embodiments, such feature can be combined with one or more other features of the other implementations/embodiments as can be desired or advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only.

The invention claimed is:

1. A method of performing radiographic examination of an object using a radiographic CT imaging system, the radiographic CT imaging system including a plurality of x-ray sources fixed to a ring each aimed at an imaging axis at a center of the ring and a corresponding ring of collimators about the imaging axis, the plurality of x-ray sources each having one collimator from the ring of collimators positioned adjacent thereto to collimate an x-ray beam emitted therefrom, and including a detector to revolve about the imaging axis to receive the collimated x-ray beams from the plurality of x-ray sources, the radiographic examination method comprising:

positioning the object at the imaging axis and performing a first scan of the object including sequentially firing the plurality of x-ray sources at a first angular speed to acquire first CT projection data of a first field of view (FOV) of the object using the collimated x-ray beams emitted from the plurality of x-ray sources that impinge upon the revolving detector;

identifying a region of interest within the first FOV;

performing a second scan of the object by sequentially firing the plurality of x-ray sources at a second angular speed faster than the first angular speed to acquire second CT projection data of a second FOV of the object smaller than the first FOV including the region of interest within the first FOV, including more narrowly collimating the x-ray beams emitted by each of the plurality of x-ray sources using the collimator in the ring of collimators positioned adjacent thereto, revolving the detector at the second angular speed, and using the narrower x-ray beams from the plurality of x-ray sources that impinge upon only a portion of the detector; and outputting the first CT projection data and the second CT projection data from the detector.

2. The method of claim 1, further comprising moving the plurality of x-ray sources relative to the object before acquiring the second FOV of the object in the second scan, including aligning the plurality of x-ray sources to the region of interest.

3. The method of claim 1, further comprising moving the object relative to the plurality of x-ray sources and the detector before performing the second scan.

4. The method of claim 1, further comprising outputting the first CT projection data and the second CT projection data (i) wirelessly during each of the first scan and the second scan, or (ii) wirelessly after each of the first scan and the second scan.

5. The method of claim 1, further comprising imaging a contrast agent flowing within the object during the first scan in order to quantitatively measure a contrast agent uptake into the object and outflow out of the object during the second scan, including repeatedly performing the second scan at prescribed time intervals.

6. The method of claim 5, further comprising sequentially firing the plurality of x-ray sources at different energy levels during the second scan.

7. The method of claim 1, further comprising sequentially firing at least 300 x-ray sources at the first angular speed around the entire ring.

8. The method of claim 7, further comprising positioning at least 300 collimators each adjacent to one of the at least 300 x-ray sources.

9. A radiographic CT imaging system, comprising:

a ring shaped imaging assembly comprising:

a plurality of stationary x-ray sources fixed in a 360 degree circular array on a ring in the ring shaped imaging assembly, each of the plurality of x-ray sources aimed toward a central axis of the ring for sequentially emitting x-rays toward an object placed at the central axis;

a radiographic detector for revolving around the central axis of the ring in the ring shaped imaging assembly at a first angular speed equivalent to a first speed of a sequential firing of the circular array of stationary x-ray sources to capture radiographic images of the object placed at the central axis; and a plurality of adjustable collimators arranged in a ring about the central axis of the ring of x-ray sources, the plurality of adjustable collimators each positioned adjacent to one of the plurality of x-ray sources to collimate an x-ray beam emitted therefrom;

wherein the plurality of stationary x-ray sources, the detector and the plurality of adjustable collimators are used to obtain radiographic images of a first field of view (FOV) of the object using first collimated x-ray beams from the circular array of x-ray sources that impinge on the detector and to obtain radiographic images of a second smaller FOV of the object using second narrower collimated x-ray beams from the circular array of x-ray sources that impinge on the detector, and wherein the detector is revolved at a second angular speed faster than the first angular speed to match a second speed of the sequential firing of the circular array of stationary x-ray sources faster than the first speed to obtain the radiographic images of the second smaller FOV of the object placed at the central axis.

10. The radiographic CT imaging system of claim 9, wherein the ring shaped imaging assembly is movable relative to the first FOV.

11. The radiographic CT imaging system of claim 9, wherein the radiographic CT imaging system is operable in a first volumetric radiographic imaging mode, a second general radiographic imaging mode, or a third fluoroscopic radiographic imaging mode.

12. The radiographic CT imaging system of claim 9, wherein the detector is configured to output captured radiographic images of the object (i) wirelessly while obtaining the radiographic images of the first field of view (FOV) of the object, or (ii) wirelessly after obtaining the radiographic images of the first field of view (FOV) of the object.

13. The radiographic CT imaging system of claim 9, wherein the ring shaped imaging assembly further comprises at least 300 x-ray sources fixed in the 360 degree circular array on the ring in the ring shaped imaging assembly, the at least 300 x-ray sources each having an adjustable collimator positioned adjacent thereto.

* * * * *